United States Patent [19]

Ronn

[11] Patent Number: 5,742,380
[45] Date of Patent: Apr. 21, 1998

[54] PLASMA ASSAY SPECTROMETER

[76] Inventor: Avigdor M. Ronn, 27A Bond St., Great Neck, N.Y. 11021

[21] Appl. No.: 777,815

[22] Filed: Dec. 31, 1996

[51] Int. Cl.$^6$ ............................................. G01N 21/64
[52] U.S. Cl. ..................... 356/39; 250/458.1; 250/459.1
[58] Field of Search ............... 356/39, 417; 250/458.1, 250/459.1

[56] References Cited

U.S. PATENT DOCUMENTS

| | | | |
|---|---|---|---|
| 4,291,230 | 9/1981 | Heiss | 250/458.1 |
| 5,205,291 | 4/1993 | Potter | 128/654 |
| 5,533,508 | 7/1996 | Doiron | 250/458.1 |

*Primary Examiner*—Vincent P. McGraw
*Attorney, Agent, or Firm*—Christopher R. Pastel; Shu M. Lee

[57] ABSTRACT

A fluorescence spectrometer for determining a concentration of a photosensitizing drug in a patient, for PhotoDynamic Therapy treatment of the patient by a treatment light at a treatment light wavelength, the fluorescence spectrometer comprising a light source that directs an interrogation beam at a blood or blood plasma sample at an interrogation wavelength range bluer than the treatment light wavelength, measuring a magnitude of an emission signal at the treatment light wavelength, the emission signal caused by the irradiation of the sample, and comparing the measured magnitude to a magnitude/concentration calibration curve to determine the concentration of the photosensitizing drug. A CPU controls the components and makes the comparison and determination.

12 Claims, 1 Drawing Sheet

PLASMA ASSAY SPECTROMETER

BACKGROUND

This invention is directed to a simple desk-top fluorescence spectrometer for assaying a drug in blood plasma. In particular, this invention is directed to a fluorescence spectrometer for assaying a photosensitizing drug in blood plasma rapidly through the use of fluorescence.

One known treatment for illnesses such as carcinomas and tumors is PhotoDynamic Therapy (PDT). PDT is presently used as primary or adjunctive treatment for benign or malignant tumors. PDT is based on activation, by light, of the photosensitive drug that is in the patient. The treatment involves the introduction of a photosensitive drug into a patient. Typically, the drug is disproportionately concentrated in the target abnormal cells. Such concentrating of the photosensitive drug causes a photosensitization of the patient. In particular, the target abnormal cells are photosensitized more than normal cells.

Accordingly, a source of light is shone at the patient, usually locally directed at the tumor composed of target abnormal cells. The light is tailored to the drug in order to cause a response of the drug to the light. The response of the drug, generally a chemical activation, causes a cascade of events that eventually results in the destruction of the tumor, often by the disruption of the target abnormal cell.

PDT can be given on an ambulatory basis and is often non-invasive. As such, the therapy can significantly reduce the high cost of more traditional treatments and eliminate the long term and often disabling side effects associated with such traditional treatments as radical surgery, radiotherapy, and chemotherapy.

PDT requires the concerted action of a sensitizing drug and an activating light. Neither component alone, as used in PDT, can cure the tumor or harm the healthy tissue. However, with the two components together, the technique powerfully destroys tumor cells selectively. There has been extensive development of technological improvements in both light sources and novel photochemical sensitizers such that commercially available high power compact lasers are used with drugs with improved tumor tissue to healthy tissue selectivity. Further, drugs having shorter half lives are continuing to be developed in order to minimize the time a patient is hyper photosensitive. Such photosensitivity often prevents a patient from outdoor activity because of extreme sensitivity to daylight.

Clinically, the PDT treatment comprises giving a particular chosen photosensitizing drug that is usually injected into the patient. A given delay time period specific to the particular drug is allowed to elapse. The time delay period allows the drug to reach the tumor tissue for light activation. The selective retention of the drug in the tumor tissue, as compared to healthy surrounding tissue, allows the eradication of the tumor tissue with minimal damage to healthy tissue.

However, the dose of the drug must be carefully monitored in order to prevent the normal cells from developing a concentration of the photosensitive drug that would photosensitize such normal cells to the light dose. Similarly, the light dose must be set high enough to cause the target abnormal tumor cells to be destroyed with minimal damage to normal cells.

Each patient has an individual metabolic rate, body mass, fluid content, and cellular dynamics such that the concentration of the photosensitizing drug in the patient cannot be accurately determined without actual measurement. The concentration of the photosensitizing drug in the blood plasma is a reliable indicator of the amount of drug that the cells have taken up. The cells take up each particular drug up to a certain known threshold concentration for each particular drug. Above a certain known maximum concentration for each particular drug, the concentration of the drug is too high in the normal cells, thus causing unacceptable damage to normal cells. The blood plasma level therefore is an accurate indicator of when the amount of photosensitizing drug is correct for PDT.

Accordingly, the total content of the photosensitizing drug in the patient's blood plasma must be determined in order that the dose of light be calculated for each patient for a given particular drug. However, current wet chemical or chromatographic techniques for assaying the content of a drug in plasma takes too long for effective PDT use. The concentration of drug can easily change considerably in the time it takes to assay by conventional techniques. Furthermore, the conventional assaying techniques are expensive, demanding extensive laboratory and technical personnel support.

OBJECTS AND SUMMARY OF THE INVENTION

It is an object of the present invention to provide a fluorescence spectrometer to assess a patient's total content of a photosensitizing drug in his plasma as rapidly as possible.

It is an object of the present invention to provide a fluorescence spectrometer that quickly assesses a patient's total content of a photosensitizing drug so that a clinician delivering PDT can adjust the light dosage so as to provide a light drug dose that will provide total efficacy.

It is an object of the present invention to provide a fluorescence spectrometer that monitors the fluorescence of a photosensitizing drug used in PhotoDynamic Therapy from a blood plasma sample, at the treatment light wavelength associated with the photosensitizing drug's use in PhotoDynamic Therapy, by exciting the blood plasma sample at a light wavelength shorter than the treatment light wavelength in order to assay the amount of the drug in the blood plasma sample. The assay amount is directly correlated with the amount of photosensitizing drug in a patient from which the blood sample was taken.

Briefly stated, a fluorescence spectrometer for determining a concentration of a photosensitizing drug in a patient, for PhotoDynamic Therapy treatment of the patient by a treatment light at a treatment light wavelength, the fluorescence spectrometer comprising a light source that directs an interrogation beam at a blood or blood plasma sample at an interrogation wavelength range bluer than the treatment light wavelength, measuring a magnitude of an emission signal at the treatment light wavelength, the emission signal caused by the irradiation of the sample, and comparing the measured magnitude to a magnitude/concentration calibration curve to determine the concentration of the photosensitizing drug. A CPU controls the components and makes the comparison and determination.

According to an embodiment of the present invention, there is provided a fluorescence spectrometer for determining a concentration of the photosensitizing drug in the patient for PhotoDynamic Therapy treatment of the patient by a treatment light at a treatment light wavelength, the fluorescence spectrometer comprising a CPU having a stored calibration curve for the photosensitizing drug that correlates on a one-for-one basis a measured emission light intensity with a calculated concentration of the photosensitizing drug, a light source, a sample holder, a detector, means for directing an interrogation light output from the light source to the sample holder, means for directing an emissions light output from the sample holder to the detector, means for measuring an intensity of the emission light output to produce the measured emission light intensity, means for inputting the measured emission light intensity to the CPU, means for comparing the measured emission light intensity to the stored calibration curve to produce a calculated concentration of the photosensitizing drug, and means for displaying the calculated concentration of the photosensitizing drug.

According to another embodiment of the present invention, there is provided a fluorescence spectrometer for determining a concentration of the photosensitizing drug in the patient for PhotoDynamic Therapy treatment of the patient by a treatment light at a treatment light wavelength, the fluorescence spectrometer comprising a CPU, a calibration curve for the photosensitizing drug that correlates on a one-for-one basis a measured emission light intensity with a calculated concentration of the photosensitizing drug, a means for transiently storing the calibration curve for access by the CPU to produce a transient calibration curve, a light source, a sample holder, a detector, means for directing an interrogation light output from the light source to the sample holder, means for directing an emissions light output from the sample holder to the detector, means for measuring an intensity of the emission light output to produce the measured emission light intensity, means for inputting the measured emission light intensity to the CPU, means for comparing the measured emission light intensity to the transiently stored calibration curve to produce a calculated concentration of the photosensitizing drug, and means for displaying the calculated concentration of the photosensitizing drug.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
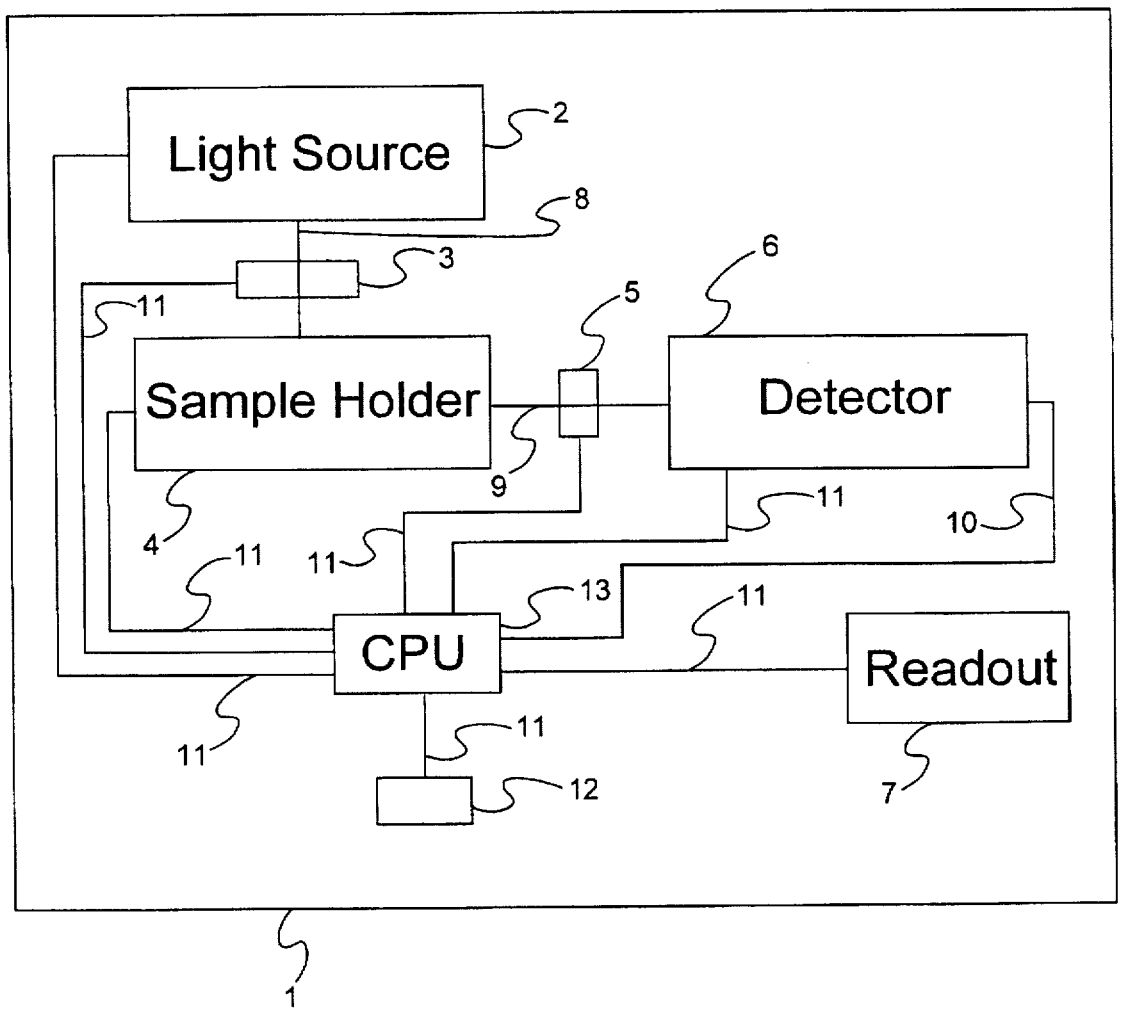
FIG. 1 is a diagram representing the fluorescence spectrometer of the present invention.

The fluorescence spectrometer of the present invention utilizes a simple fluorescence apparatus which allows a near instant readout. The fluorescence spectrometer incorporates a light source which is selectively tuned to a given wavelength range needed to excite the drug used for a particular PDT. This technique is effective for drugs under all conventional PDT methodologies or new methodologies because inherent in PDT methodologies is the requirement that the drugs used be sensitive to light.

Further, the treatment light wavelength is typically at the red region of the visible spectrum because tissue transmission of visible light is best at the red region. The interrogation light is set by examination of the visible (ultraviolet to near infrared) absorption spectrum of the particular drug being used for PDT. The interrogation light is set to an absorption band, in the absorption spectrum, of higher energy (to the blue side) of the treatment wavelength. The interrogation light is preferably of the wavelength range that is full width half height of the absorption feature of the absorption curve of the PDT drug.

The interrogation light causes the sample to emit an emission signal light, for example by fluorescence, at a lower wavelength than the interrogation light. The emission signal light is collected and its intensity measured.

The emission signal light can be measured at different wavelengths that can be determined through examination of the spectral emission curves for each particular PDT drug in order to determine the effective emission signal wavelength. However, such preparation is not necessary because the fluorescence spectrometer of the present invention uses the very same wavelength that will be used for the PhotoDynamic Therapy itself as the effective emission signal wavelength. Therefore, all drugs used in PDT are easily and effectively assayed by the fluorescence spectrometer of the present invention.

Referring to FIG. 1, in the fluorescence spectrometer 1 of the present invention a light source 2 is connected to a sample holder 4 by a light guide 8 which has a variable filter element 3 in the light path of light guide 8. The emission light from the sample in sample holder 4 is collected at an off-angle such as 90 degrees and directed by an emissions light guide 9 to a detector 6. An emissions variable filter element 5 is in the light path of emissions light guide 9.

Detector 6 is connected by a cable 10 to a CPU 13 which has an input 12 and a readout 7. CPU 13 has a plurality of I/O control paths 11 which controls light source 2, variable filter element 3, sample holder 4, emissions variable filter element 5, detector 6, readout 7, and input 12.

In response to input 12, CPU 13 consults a database for the particular PDT photosensitizing drug being used, loads the treatment light wavelength for the particular PDT photosensitizing drug and directs emissions variable filter element 5 to pass through the loaded treatment light wavelength. CPU 13 also loads the absorption feature of the particular photosensitizing drug that is to the blue of the treatment light and directs variable filter element 3 to pass through the wavelength band corresponding to the selected absorption feature. CPU 13 also loads the calibration database for the selected photosensitizing drug into memory. CPU checks for a sample in sample holder 4, and directs light source 2 to send light to sample holder 4.

Emission passing through emissions variable filter 5 is measured by detector 6 which sends the data to CPU 13. CPU compares the detector 6 data to the calibration database and sends the concentration of the photosensitizing drug calculated to readout 7.

The system is then reset for next analysis. Optionally, the calculations can be stored for further future use. Light source 2 can be any convenient broadband light source such as, for example, a rare gas discharge lamp, a high energy incandescent light source, or an electric arc lamp. Lasers can also be used. In one embodiment, a filtered Zeiss illuminator was used. It is most preferred that the CPU controls the peripheral components of the entire fluorescence spectrometer of the present invention. It is less preferred to allow control of less than all the components peripheral to the CPU by the CPU.

Variable filter 3 can be any convenient means for controlling a wavelength range of a beam of light such as, for example, a dichroic filter of a varying wavelength gradient, a series of bandpass filters, or a dispersive element such as a grating. In one embodiment, a Schott glass filter was used. Emissions variable filter 5 similarly can be any convenient means for controlling a wavelength range of a beam of light such as, for example, a dichroic filter of a varying wavelength gradient, a series of bandpass filters, or a dispersive element such as a grating.

Variable filter 3 will generally be passing through a broader bandpass than emissions variable filter 5 because variable filter 3 is for the interrogation light which only needs to pump energy into the photosensitizing drug. Variable filter 3 is preferably a filter that passes through a wavelength band corresponding to full width half height (FWHH) of an absorption feature to the blue (higher energy) of the PDT treatment wavelength. Emissions variable filter 5 is generally in the red region because the PDT treatment light wavelength is generally in the red region in accordance with the generally red bandpass of tissue. Emissions variable filter is preferably a filter that passes through the PDT treatment wavelength and about 10 nm to each side of the PDT treatment wavelength.

The sample can be produced by any convenient means such as taking a small amount, for example 2 ml, of blood is from the patient. The blood is centrifuged at a convenient time and spin rate effective to separate the plasma, for example at 2000 RPM for 10 minutes. The supernatant which is the plasma is pipetted out and diluted with sterile unbuffered saline (isotonic 0.15M). In the case of the PDT drug Foscan®, the supernatant is diluted by a factor of 100. The diluted sample is then introduced directly to sample holder 4 for analysis.

Other drugs might require dilution factors other than the 100 for the PDT drug Foscan® that will bring the fluorescence signal into acceptable fluorimetry range. The dilution factor is effective to cause the diluted sample to emit a measurable emission signal at the treatment light wavelength when irradiated by the interrogation wavelength range at an absorption band bluer than the treatment light wavelength.

The dilution factor is effective when the signal magnitude range that corresponds to a concentration range that includes the treatment concentration includes a low signal that is strong enough to detect reliably above the baseline and a high signal that is not so strong as to overload the detection equipment. One of ordinary skill can easily determine, without extensive experimentation, the dilution factor needed for a particular drug. One easy technique is to make dilutions of different factors of ten (such as 0, 10, 100, 1000) and determine which factor produces fluorescence signals appropriate for the equipment.

In another method to produce a sample for analysis, a drop of blood is diluted by a calibrated amount of unbuffered saline solution. The diluted whole blood sample is introduced to sample holder 4 for analysis. The emission signal is compared to a calibration curve for the particular photosensitizing drug in diluted whole blood.

In another method to produce a sample for analysis with the device of the present invention, a specific small sample of tissue such as for example, 10 mg of tissue, is frozen and powderized. The powderized tissue is extracted with a solvent effective to extract the particular photosensitizing drug from the powderized tissue. For the drug Foscan®, 1 ml of DMSO was used as the extracting solvent. The extract is introduced to sample holder 4 for analysis. The emission signal is compared to a calibration curve for the particular photosensitizing drug in the solvent.

In the fluorescence spectrometer of the present invention, an interrogation light source is tuned by variable filter 3 to the excitation wavelength range of an absorption feature of the PDT photosensitive drug. The light is directed towards sample holder 4 containing the diluted plasma sample. The sample holder can be any convenient form that contains the sample while remaining transparent to the filtered light source and the emissions wavelength such as, for example, a cuvette.

As recited above, the excitation wavelength is an absorption wavelength to the blue of the wavelength that is used for PhotoDynamic Therapy for the particular drug. The bandpass filters should preferably pass through the full width half height of the absorption feature of the absorption curve of the PDT drug. If a monochromator is used, it should be set to the peak of the absorption feature. Such optics for the variable filters 3 and 5 can include lenses and prisms to spread and collimate the beam, particularly if the interrogation beam is a laser beam.

The emission signal is collected at an off-angle, such as 90 degrees, from the interrogation light path and modified by optical components in emissions variable filter 5 of the present invention. The emission signal wavelength is the same wavelength as that used for the PhotoDynamic Therapy. The optics include a bandpass filter or a monochromator in order to pass through the wavelength of the PhotoDynamic Treatment light. The optics serve also to block the wavelengths of interrogation light.

CPU 13 controls the other components by any convenient control software. The filters can be mounted on any convenient motorized stage controlled by CPU 13, the sample holder can include a safety lockout to prevent the light being turned on by CPU 13 when the holder is exposed to the operator.

The emission signal light is detected by detector 6 which collects the emission from the sample at the PhotoDynamic Therapy treatment wavelength. Detector 6 also includes such electronics as bias components, preamplifiers, amplifiers, or power source. In one embodiment, a photodiode was used.

The apparatus is calibrated by preparing a calibration curve from standard solutions prepared of the particular drug being used for PDT. The emissions signal for each prepared solution is plotted against the known concentration of the prepared solution. The calibration curve is prepared and entered into a database in the memory of CPU 13. CPU also includes related necessary components such as a power source.

The signal intensity from is compared with the calibration curve by CPU 13. The result is presented in readout 7 by any convenient means such as being a point on the calibration curve displayed on a CRT, a readout on a digital voltmeter, or as a number shown on a paper printout.

In all cases, the fluorescence spectrometer of the present invention quickly and effectively determined the concentration of any PDT drug tested.

It can be seen that the fluorescence spectrometer of the present invention relies on only one aspect for its efficiency, accuracy, and precision. That is that the apparatus must be calibrated, prior to clinical measurement, with known solutions of the same photosensitizing drug that is being used for the PDT treatment. As recited above, a calibration curve is prepared from the standard solutions and is used to read off the exact concentration of the patient's plasma sample. A typical assay would take less than twelve minutes from the time of drawing of the blood sample to the reporting of the drug concentration from the readout of the present invention.

There are a number of known ways to prepare a calibration curve with precision. For example, the emission strength/drug concentration points can be plotted on graph paper. Another example is to statistically set a calibration curve in the computer of the fluorimeter so that the calibration curve is directly accessed from the instrument's interface. Serial dilution of the sample increases precision.

The fluorescence spectrometer of the present invention has been tested a number of times on both animal and human plasma samples, utilizing a modified conventional spectrofluorimeter as well as a custom made solid state single frequency device and has been found to be reliable, repeatable, and accurate down to doses as low as picograms/milliliters. This sensitivity is thousands of times more than that necessary to assay human plasma samples which, for the drugs presently available, normally range from hundreds of nanograms to micrograms per milliliter.

The dilution factor is easily adjusted for drugs that produce higher dose concentrations by increasing the dilution. The dilution similarly can be decreased to accommodate new drugs that require very low dose concentrations. Future drugs that perhaps require extremely low dose concentrations can be accommodated by a negative dilution—that is, the volume of plasma can be reduced by evaporation, distillation, filtration, resin exchange, or other common techniques known to chemists and technicians.

The fluorescence spectrometer of the present invention will work even when the particular drug does not require dilution. The fluorescence spectrometer of the present invention will work even if the interrogation light is a light source such as a laser or monochrome light source that does not require filtration before being directed at the blood plasma sample. In such cases, variable filter 3 is wide open or omitted.

Although the present fluorescence spectrometer will give a fast and accurate assay in one run, good clinical practice can require two or more determinations in order to have verification of the initial measured value.

Having described preferred embodiments of the invention with reference to the accompanying drawing, it is to be understood that the invention is not limited to those precise embodiments, and that various changes and modifications may be effected therein by one skilled in the art without departing from the scope or spirit of the invention as defined in the appended claims.

What is claimed is:

1. A fluorescence spectrometer for determining a concentration of the photosensitizing drug in the patient, for PhotoDynamic Therapy treatment of the patient by a treatment light at a treatment light wavelength, said fluorescence spectrometer comprising:

a CPU having a stored calibration curve for the photosensitizing drug that correlates on a one-for-one basis a measured emission light intensity with a calculated concentration of the photosensitizing drug;

a light source;

a sample holder;

a detector;

means for directing an interrogation light output from said light source to said sample holder;

means for directing an emissions light output from said sample holder to said detector;

means for measuring an intensity of said emission light output to produce said measured emission light intensity;

means for inputting said measured emission light intensity to said CPU;

means for comparing said measured emission light intensity to said stored calibration curve to produce a calculated concentration of the photosensitizing drug; and means for displaying said calculated concentration of the photosensitizing drug.

2. A fluorescence spectrometer according to claim 1 further comprising a means for modifying said interrogation light to a band of wavelengths corresponding to an absorption feature of the photosensitizing drug bluer than the PhotoDynamic Therapy treatment wavelength.

3. A fluorescence spectrometer according to claim 2 wherein said means for modifying said interrogation light includes a filter which passes a range of wavelengths corresponding to full width half height of said absorption feature of the photosensitizing drug.

4. A fluorescence spectrometer according to claim 1 further comprising a means for modifying said emission light output to corresponds to the PhotoDynamic Therapy treatment wavelength.

5. A fluorescence spectrometer according to claim 4 wherein said means for modifying said emission light output includes a filter which passes said PhotoDynamic Therapy treatment wavelength and wavelengths up to about 10 nm to the high energy side and about 10 nm to the low energy side of said PhotoDynamic Therapy treatment wavelength.

6. A fluorescence spectrometer according to claim 1 further comprising a means for controlling at least one of said light source, said sample holder, said detector, said means for directing an interrogation light output, said means for directing an emissions light output, said means for measuring, means for inputting, and said means for comparing; wherein said means for controlling is by said CPU.

7. A fluorescence spectrometer for determining a concentration of the photosensitizing drug in the patient, for PhotoDynamic Therapy treatment of the patient by a treatment light at a treatment light wavelength, said fluorescence spectrometer comprising:

a CPU;

a calibration curve for the photosensitizing drug that correlates on a one-for-one basis a measured emission light intensity with a calculated concentration of the photosensitizing drug;

a means for transiently storing said calibration curve for access by said CPU to produce a transient calibration curve:

a light source;

a sample holder;

a detector;

means for directing an interrogation light output from said light source to said sample holder;

means for directing an emissions light output from said sample holder to said detector;

means for measuring an intensity of said emission light output to produce said measured emission light intensity;

means for inputting said measured emission light intensity to said CPU;

means for comparing said measured emission light intensity to said transiently stored calibration curve to produce a calculated concentration of the photosensitizing drug; and means for displaying said calculated concentration of the photosensitizing drug.

8. A fluorescence spectrometer according to claim 7 further comprising a means for modifying said interrogation light to a band of wavelengths corresponding to an absorption feature of the photosensitizing drug bluer than the PhotoDynamic Therapy treatment wavelength.

9. A fluorescence spectrometer according to claim 8 wherein said means for modifying said interrogation light includes a filter which passes a range of wavelengths corresponding to full width half height of said absorption feature of the photosensitizing drug.

10. A fluorescence spectrometer according to claim 7 further comprising a means for modifying said emission light output to corresponds to the PhotoDynamic Therapy treatment wavelength.

11. A fluorescence spectrometer according to claim 10 wherein said means for modifying said emission light output includes a filter which passes said PhotoDynamic Therapy treatment wavelength and wavelengths up to about 10 nm to the high energy side and about 10 nm to the low energy side of said PhotoDynamic Therapy treatment wavelength.

12. A fluorescence spectrometer according to claim 7 further comprising a means for controlling at least one of said light source, said sample holder, said detector, said means for directing an interrogation light output, said means for directing an emissions light output, said means for measuring, means for inputting, and said means for comparing; wherein said means for controlling is by said CPU.

* * * * *